United States Patent [19]

Winslow, Jr.

[11] 4,043,178
[45] Aug. 23, 1977

[54] HYDROGEN PROBE SYSTEM
[75] Inventor: Joseph D. Winslow, Jr., Houston, Tex.
[73] Assignee: Petrolite Corporation, St. Louis, Mo.
[21] Appl. No.: 683,878
[22] Filed: May 6, 1976
[51] Int. Cl.$^2$ ............................................. G01N 7/10
[52] U.S. Cl. .................................... 73/23; 23/253 C
[58] Field of Search ................ 73/19, 23; 23/230 C, 23/232 R, 232 E, 253 C, 254 R, 254 E; 55/158, 270

[56] References Cited

U.S. PATENT DOCUMENTS

| | | | |
|---|---|---|---|
| 2,280,086 | 4/1942 | Hayward | 73/19 |
| 2,671,336 | 3/1954 | Hulsberg | 73/19 |
| 3,949,593 | 4/1976 | Oertle | 73/19 |

*Primary Examiner*—S. Clement Swisher
*Assistant Examiner*—Stephen A. Kreitman
*Attorney, Agent, or Firm*—Sidney B. Ring; Hyman F. Glass

[57] ABSTRACT

A hydrogen probe system measuring hydrogen gas produced in the corrosion of steel, both in volume and rate, with a relatively simple construction, rapid installation at any location and trouble-free operation for extended periods of time without supervision. The probe system has a ferrous metal body enclosing a cavity collecting hydrogen gas metered through a capillary port into a background liquid contained in a sample cell thereby forming discrete, uniform-dimensioned bubbles. A detector senses the release of these bubbles and provides a representative output signal to an output means giving a readout of the hydrogen gas bubbles being released within a selected time interval.

17 Claims, 3 Drawing Figures

HYDROGEN PROBE SYSTEM

BACKGROUND OF THE INVENTION

1. Field of the Invention

This invention relates to measuring and testing of corrosion processes, and it relates more particularly to a probe system for measuring molecular hydrogen gas created by the corrosion of ferrous metals.

2. Description of the Prior Art

It is often desirable to determine the rates at which ferrous metals corrode with a corrodant, such as a corrosive aqueous liquid. For example, corrosion inhibitors are added to aqueous liquids to reduce the corrosion of exposed metals. Instruments are used to measure the rates at which these metals corrode so that the effectiveness of inhibitor addition can be determined. One measurement of the rate of corrosion upon ferrous metals involves the determination of the amount of molecular hydrogen created by the corrosion reaction of a ferrous metal exposed to a corrodant. For example, a steel sidewall of a pipeline carrying a corrodant, such as hydrogen sulfide in water, has a corrosion reaction creating atomic hydrogen which diffuses through the sidewall and released exteriorly as molecular hydrogen gas. Escape of the molcular hydrogen gas from the sidewall permits the corrosion reaction to continue. However, the molecular hydrogen gas escaping the sidewall can oftentimes build up to a sufficient pressure causing physical injury such as blistering and rupturing of the sidewall's exterior surface.

Various measurement systems have been proposed for the measurement of the molecular hydrogen gas produced by the corrosion reaction. For this purpose, a probe may be inserted through the sidewall of the pipeline and arranged to measure the molecular hydrogen gas pressure buildup within the probe. For this purpose, the probe has a ferrous metal body in which there is formed a cavity. The corrosion reaction produced by the corrodant surrounding the probe causes molecular hydrogen gas to accumulate within the cavity. A pressure gauge mounted atop the probe indicates the actual pressure of the hydrogen gas accumulating within the cavity. For example, in very active corrodants, the pressure buildup of such a probe can reflect hydrogen gas accumulations within the cavity from an initial 15 psi to about 100 psi within a 24-hour period. The probe carries a manual venting valve so that the pressure can be released from the cavity when the pressure limits of the gauge are reached. Thus, this type of hydrogen measurement probe must be employed in a supervised manner wherein the operator can periodically record the readings of the probe and also vent hydrogen gas as necessary to prevent the destruction of the pressure gauge. This type of hydrogen measurement probe is simple and relatively inexpensive but has not found extensive utilization in the industry because of the requirement for relatively constant supervision.

Another type of hydrogen measurement probe avoids the supervision problem but employs a sophisticated gas ionization instrumentation principle. In this probe, the hydrogen gas is vented in a relatively continuous manner from the cavity within the probe body. The vented gas flows through an ionization chamber and detector sensor whose output is measured upon a scalar instrument indicating both total gas volume and rate of gas flow. This probe and readout instrumentation is relatively accurate, very expensive and dependable, but requires careful calibration and complicated installation. Also, this probe is relatively delicate for use unattended within oil fields, refineries and chemical plants.

The hydrogen probe system of the present invention is arranged to provide the simplicity of construction and operation of first mentioned probe with the utility and accuracy of the second mentioned hydrogen measurement probe but without its great expense and other accompanying problems.

SUMMARY OF THE INVENTION

In accordance with this invention, there is provided a hydrogen probe system having a ferrous metal body with an enclosed fluid-tight internal cavity collecting hydrogen gas produced by action of a corrodant on the body. The hydrogen gas within the cavity is passed by a fluid channel through a capillary port into a background liquid in a sample cell thereby forming discrete uniform-dimensional bubbles. Detector means sense the bubbles being released into the background liquid and provide a representative output signal. The output signal is received in an output means which provides a readout of the hydrogen gas bubbles being released within a selected time interval. In a preferred embodiment, the output means includes a totalizer for indicating the total number of bubbles released in the selected time and a differentiator for indicating the rate of bubble release.

DESCRIPTION OF SPECIFIC EMBODIMENTS

Figure 1:
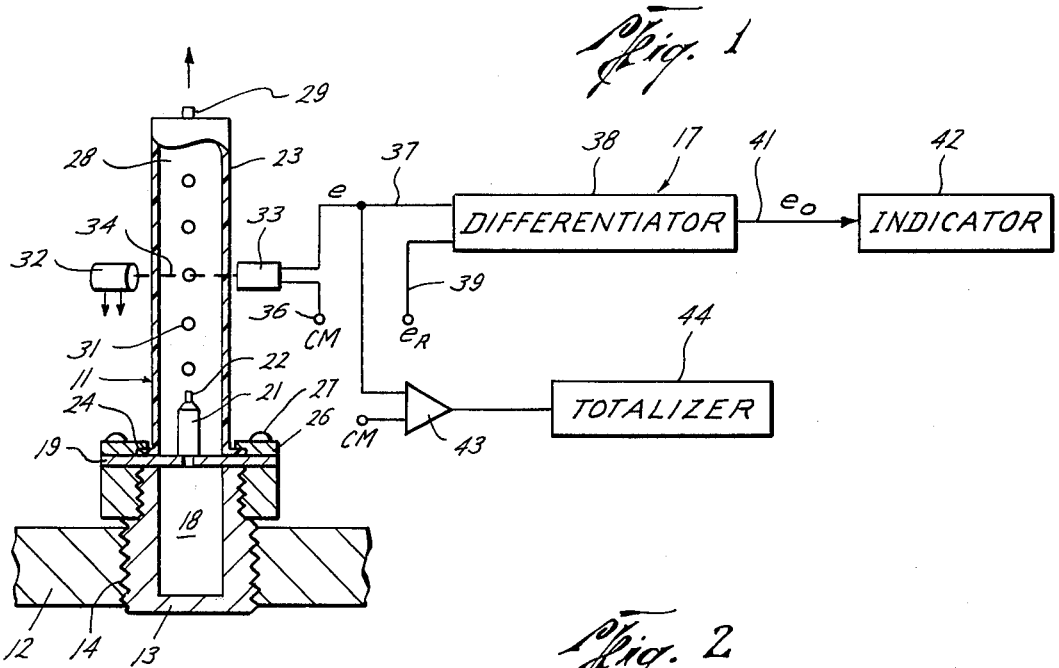
FIG. 1 is a vertical section and an electrical schematic in illustration of one embodiment of the hydrogen probe system of the present invention.

FIG. 1 illustrates one embodiment of the hydrogen probe system 11 of the present invention. The system 11 is threadedly secured into a pipe wall 12 with the body 13 exposed to a corrodant, such as an aqueous stream containing hydrogen sulfide. The pipe wall 12 can be the steel sidewall of an exposed pipeline. The body 13 can be a pipe plug with threads 14 for threadedly engaging the pipe wall 12. Other arrangements for adapting the body 13 to the exposure of a corrodant may be employed, if desired. The probe system 11 is comprised basically of the body 13, a sample cell 16 and instrumentation circuitry 17.

The body 13 is provided with a cavity 18 in which the hydrogen gas is collected, preferably under superatmospheric pressure. The upper portion of the cavity 18 is closed by a metal plate 19. The plate 19 carries a capillary outlet tube 21 which is a fluid channel provided at its extremity remote from the cavity 18 with a capillary port 22. The port 22 is dimensioned so that a metered release of the hydrogen gas accumulating in the cavity 18 is provided at some suitable rate of release. The port 22 can be sized so that there is always a superatmospheric pressure of hydrogen in the cavity 18, but yet such pressure does not rupture the probe system 11. Mounted atop the plate 19 is a sample cell 23 which may take the form of an upright cylindrical tube of a material that is transparent to energy sources used for bubble detection purposes.

Preferably, the cell 23 is a tube of transparent material such as acrylic polymers or glass. The cell 23 has a lower flange 24 secured beneath a collar 26 by screws 27. With this arrangement, a fluid-tight interconnection is made between the lower portion of the cell 23 and the body 13. The cell 23 is filled with background liquid that is chemically inert and in which hydrogen gas has a relatively low solubility. For example, the background liquid can be a silicone oil or a liquid selected from the group consisting of diethylene glycol, propylene glycol and mixtures thereof. The relative composition of the background liquid 28 is relatively unimportant as long as it can function properly within the cell 23. The cell 23 carries at its uppermost portion a small vent 29 through which hydrogen gas escapes and through which the background liquid 28 may be introduced into the cell 23.

During the operation of the probe system 11, the hydrogen collected in the cavity 18 passes from the port 22 and appears as small finite bubbles 31 which stream upwardly through the background liquid 28. As will be apparent under uniform conditions in the probe system 11, these bubbles are substantially uniform in size and vary only in vertical spacing between them relative to the amount of hydrogen passing through the port 22. Stated in another manner, the vertical spacing between the bubbles 31 is directly proportional to the amount of gas vented from the cavity by the port 22. As a result, the number of bubbles per unit time is monitored to determine the rate of hydrogen gas accumulating within the probe cell 11; and also, the total number of bubbles for a selected period of time reflects that total amount of hydrogen gas from the cavity 18 passing through the port 22 into the cell 23. Any suitable means for monitoring the rate and total number of the bubbles 31 can be used in the present system.

In a preferred form, the production of the bubbles 31 is monitored by an optical system. More particularly, as shown in FIG. 1, the optical system includes a detector sensing the release of the hydrogen gas bubbles 31 into the background liquid 28 and providing an output signal e representative of such bubble release. For example, a collimating light source 32 on one side of the cell 23 and a light sensing detector 33 on the other side of the cell are aligned with the collimated light ray 34. As each bubble 31 passes through the light ray 34, the detector 33 produces an output signal e of electrical characteristic which in associated circuitry 17 produces a readout reflecting the hydrogen gas bubbles being released from the port 22.

In circuitry 17, the output 3 of the source 32 is applied between circuit common 36 and a first input 37 of a differentiator 38. The differentiator has second input 39 connected to a suitable referencing voltage $e_R$. The differentiator 38 functions in the usual manner wherein the number of bubbles 31 per unit time provides an output signal $e_o$ in output 41. The output signal $e_o$ is applied to a suitable readout device or indicator 42 such as a digital voltmeter. In this application, the indicator 42 is calibrated with a readout representing the volume per unit time of the gas bubbles 31 released from the port 22 (e.g., cubic centimeters per minute). Thus, the exact rate of hydrogen diffusing through the body 13 into the cavity 18 of the probe system 11 is precisely determined instantaneously.

In many cases, it is also desired to determine the total amount of hydrogen gas diffusing into the cavity 18. For this purpose, the output signal e of the light detector 33 is employed in an event counter or totalizer for a readout of the total number of bubbles released in a selected time period. This output signal e is applied as one input to an isolation amplifier 43 which is referenced to the circuit common. The output of the amplifier 43 in a voltage-to-current converting function is applied to an integrating circuit or totalizer 44. The totalizer 44 provides a readout of the total amount of hydrogen bubbles 31 released from the port 22. For example, the totalizer 44 resets for each 24-hour period and during each such period, the readout represents the total volume of hydrogen gas (e.g., cubic centimeters, under standard gas measurement conditions).

The detector 33 may include a temperature sensitive element 33a, such as a thermister, so that the output signal e is corrected for the effect of temperature upon the size of bubbles 31.

Figure 2:
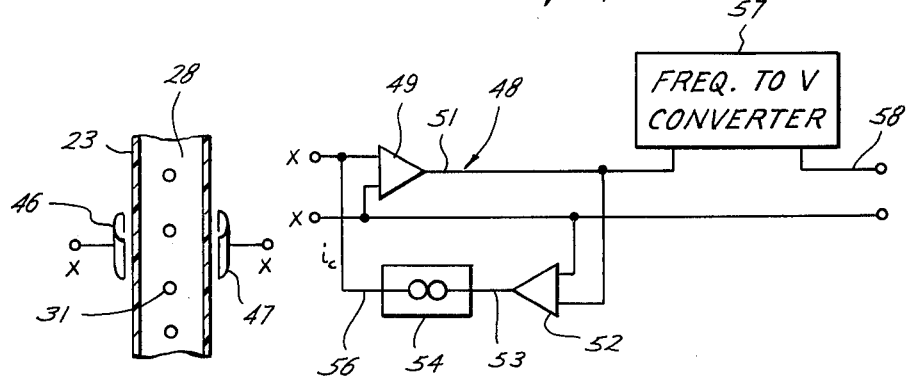
FIG. 2 is a partial illustration of another embodiment of the present probe system.

The release of the bubbles 31 from the port 22 may be determined other than optically as shown in FIG. 2. For example, the background liquid 28 may be selected to have a relatively low dielectric constant. Thus, the number of gas bubbles 31 affect the specific inductive capacity of the background liquid 28 in the cell 23. The detector for this purpose can be a pair of capacitor plates 46 and 47 which are semicylindrical in shape and positioned diammetrically opposite one another upon the cell 23. The output terminal of plates 46 and 47 are marked X and connected to the X terminals in the circuit 48 shown in FIG. 2. The circuit 48 consists of an isolation amplifier 49 have a first input to one of the plates and a second input connected to the other of the plates. The output 51 of the amplifier is in a feedback circuit through a comparator 52 whose output 53 controls a constant current generator 54. The constant current generator in its output 56 provides an output current $i_c$ which is applied to one of the plates. As the bubbles 31 pass between the plates 46 and 47, an induced change in capacitance produces an increased rate of change in the output voltate signal from the amplifier 49. This output voltage signal is applied to the comparator 52 and causes the constant current generator 54 to switch polarity between two preset voltage levels more rapidly with respect to time. Thus, bubbles 31 passing between the plates 46 and 47 represent an increasing time rate of change in polarity from the generator 54. As a result, the output voltage signal from the amplifier 49 has a voltage fluctuation whose frequency changes in inverse proportion to the capacitance change between the plates 46 and 47. These voltage variations in the output 51 are applied to a frequency-to-voltage converter 57 having an output 58 with a voltage signal that is inversely proportional to the capacitance change between the plates 46 and 47, and in direct proportion to bubble size. As a result, the voltage signal in a suitable differentiator reflects the rate of bubbles 31 released from the port 22 and also in an event counter or totalizer, the number of bubbles released. The differentiator and indicator, and totalizer can be used in circuit 48 as were employed for these purposes relative to FIG. 1.

Figure 3:
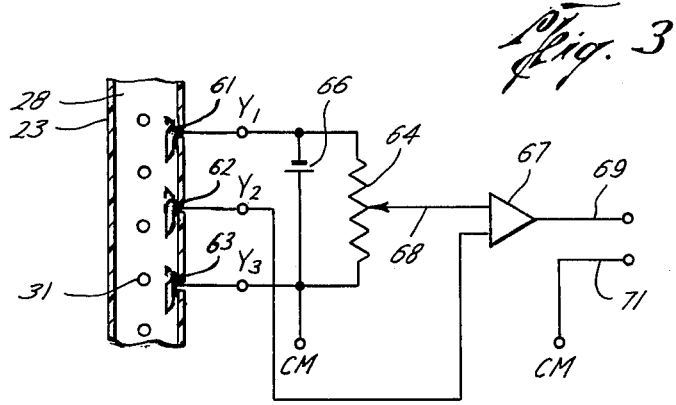
FIG. 3 is a partial illustration of a third embodiment of the present probe system.

Referring now to FIG. 3, a third embodiment of the present probe system 11 will be described which detects the release of bubbles 31 by differential conductivity effects. This system employs a detector and output means operating upon a substantial difference in the conductivity of bubbles 31 relative to the background liquid 28. Preferably, the background liquid 28 is a material having a relatively low specific resistivity relative to the hydrogen bubbles. For example, the background liquid may be diethylene glycol with a trace of water (100 ppm.). For a detector, three identical semicylindrical metal electrodes 61, 62 and 63 are spaced longitudinally along the cell 23 in contact with the background liquid. As a bubble 31 passes between the electrodes, the potential of electrode 62 changes in magnitude from a first value to a second value to a third value and then returns to the first value. This change in voltage, in a suitable output circuit, reflects the number of bubbles 31 released from port 22. For example, the electrodes 61 and 63 are connected into a bridge which has a potentiometer 64 as one arm and excited by battery 66. As a result, a potential difference existing between the electrode 62 and tap 68 of potentiometer 64 fluctuates one cycle per bubble passage. The electrode 62 is connected to a first input of a voltage amplifier 67 whose other input connects to the movable tap 68 of the potentiometer 64. With this arrangement, the output 69 of the amplifier 67 relative to circuit common 71 is a voltage which fluctuates at a frequency of one cycle per bubble 31 which passes the electrode 62. As in FIG. 1, this voltage change in output 69 can be applied to a differentiator for determining the rate of bubbles 31 passing the electrode 62 per unit time. Also, a comparator can be employed to receive the voltage change on the output 69 and drive an event counter or totalizer to produce a readout of the total number of bubbles 31 which have passed the electrode 62. Obviously, other arrangements for detecting the passage of the bubbles 31 from the port 22 and providing a readout of their rate and total number can be employed with equal facility.

Various modifications and alterations in the described hydrogen probe system will be apparent to those skilled in the art from the foregoing description which do not depart from the spirit of the invention. For this reason, these changes are desired to be included within the scope of the appended claims. The appended claims define the present invention; the foregoing description is to be employed for setting forth the present embodiments as illustrative and not limited in nature.

What is claimed is:
1. A hydrogen probe system comprising:
   a. a ferrous metal probe body adapted to be exposed to a corrodant, said body having an enclosed fluid-tight internal cavity for collecting hydrogen gas produced by action of the corrodant on said body;
   b. a sample cell containing a background liquid chemically inert and in which hydrogen has a relatively low solubility;
   c. capillary port means in said sample cell connected by a fluid channel to said cavity, and said capillary port means precisely metering discrete uniform-dimensioned bubbles of hydrogen gas into said background liquid;
   d. detector means sensing the release of hydrogen gas bubbles into said background liquid and providing an output signal representative thereof; and
   e. output means receiving said output signal and providing a readout of the hydrogen gas bubbles being released from said capillary port means.

2. The hydrogen probe system of claim 1 wherein said output means include a totalizer means for indicating the total number of hydrogen gas bubbles released into said background liquid within a selected time interval and a differentiator means for indicating the rate of hydrogen gas bubble release per unit time.

3. The hydrogen probe system of claim 1 wherein said background liquid is optically transparent and said detector means includes a light source and a light sensing element with a light ray aligned to intersect the travel of the hydrogen gas bubbles in said background liquid being released from said capillary port means.

4. The hydrogen probe system of claim 3 wherein said background liquid is selected from the group consisting of diethylene glycol, propylene glycol and mixtures thereof.

5. The hydrogen probe system of claim 1 wherein said background liquid is a dielectric material and said detector means includes capacitive elements adjacent the travel of the hydrogen gas bubbles in said background liquid being released from said capillary port means.

6. The hydrogen probe system of claim 1 wherein said readout of hydrogen gas bubbles being released is corrected for temperature variation by a temperature responsive element in said detector means or said output means.

7. The hydrogen probe system of claim 6 wherein said temperature responsive element is a thermister.

8. The hydrogen probe system of claim 1 wherein said detector means includes inductive elements adjacent the travel of the hydrogen gas bubbles in the background liquid being released from said capillary port means and the hydrogen gas bubbles have a specific inductive capacity substantially different than the background liquid.

9. The hydrogen probe system of claim 1 wherein said detector means include fluid contacting elements adjacent the travel of the hydrogen gas bubbles in the background liquid being released from said capillary port means and the hydrogen gas bubbles have a conductance substantially different from said background liquid.

10. The apparatus for a hydrogen probe system comprising:
   a. a ferrous metal probe body adapted to be exposed to a corrodant, said body having an enclosed fluid-tight internal cavity for collecting hydrogen gas produced by action of the corrodant on said body;
   b. a sample cell containing a background liquid chemically inert and in which hydrogen gas has a relatively low solubility; and
   c. capillary port means in said sample cell connected by a fluid channel to said cavity, and said capillary port means precisely metering discrete uniform-dimensioned bubbles of hydrogen gas into said background liquid.

11. The apparatus of claim 10 wherein said background liquid is optically transparent.

12. The apparatus of claim 11 which includes a detector means for sensing the release of hydrogen gas bubbles into said background liquid including a light source and a light sensing element with a light ray aligned to intersect the travel of the hydrogen gas bubbles in said background liquid being released from said capillary port means and providing an output signal representative of the release of said hydrogen gas bubbles.

13. The apparatus of claim 11 wherein said background liquid is selected from the group consisting of diethylene glycol, propylene glycol and mixtures thereof.

14. The apparatus of claim 10 wherein said background liquid is a dielectric material whose specific inductive capacity is substantially different from that of the hydrogen gas of the said hydrogen gas bubbles.

15. The apparatus of claim 14 which includes a detector means for sensing the release of hydrogen gas bubbles into said background liquid including capacitative elements adjacent the travel of the hydrogen gas bubbles in the said background liquid being released from said capillary port means and providing an output signal representative of the release of said hydrogen gas bubbles.

16. The apparatus of claim 10 in which said background liquid has a conductance substantially different from the hydrogen gas of said hydrogen bubbles.

17. The apparatus of claim 16 which includes a detector means including fluid contacting elements adjacent the travel of the hydrogen gas bubbles in the background liquid being released from said capillary port means for sensing the release of hydrogen gas bubbles into said background liquid and providing an output signal representative thereof.

* * * * *